United States Patent
Stihler

(10) Patent No.: US 9,138,548 B2
(45) Date of Patent: Sep. 22, 2015

(54) FLUID WARMER AND METHOD OF OPERATING A FLUID WARMER

(71) Applicant: Stihler Electronic GmbH, Stuttgart (DE)

(72) Inventor: Axel Stihler, Stuttgart (DE)

(73) Assignee: Stihler Electronic GmbH, Stuttgart (DE)

( * ) Notice: Subject to any disclaimer, the term of this patent is extended or adjusted under 35 U.S.C. 154(b) by 0 days.

(21) Appl. No.: 14/175,145

(22) Filed: Feb. 7, 2014

(65) Prior Publication Data

US 2014/0221960 A1    Aug. 7, 2014

(30) Foreign Application Priority Data

Feb. 7, 2013   (EP) .................................... 13154381

(51) Int. Cl.
*A61B 18/14* (2006.01)
*A61M 5/44* (2006.01)
*H05B 1/02* (2006.01)

(52) U.S. Cl.
CPC .............. *A61M 5/44* (2013.01); *H05B 1/025* (2013.01); *H05B 1/0244* (2013.01)

(58) Field of Classification Search
CPC .  A61M 5/44; A61M 5/445; A61M 2205/365; A61M 1/14; A61M 1/1601; F24H 9/2028; F24H 1/142; H05B 1/025; H05B 1/0244
USPC .............. 392/465, 466, 467, 468, 469, 470; 604/114, 113, 6.13, 291
See application file for complete search history.

(56) References Cited

U.S. PATENT DOCUMENTS

| | | | |
|---|---|---|---|
| 4,695,385 A * | 9/1987 | Boag ............................. | 210/636 |
| 5,381,510 A | 1/1995 | Ford et al. | |
| 2003/0220605 A1* | 11/2003 | Bowman et al. ................ | 604/29 |
| 2008/0021377 A1* | 1/2008 | Kienman et al. ................ | 604/29 |
| 2009/0213521 A1* | 8/2009 | Bedingfield ................... | 361/194 |
| 2010/0312161 A1* | 12/2010 | Jonsson et al. ............... | 604/5.01 |

FOREIGN PATENT DOCUMENTS

| | | |
|---|---|---|
| DE | 10 2010 036 295 A1 | 3/2012 |
| GB | 2 052 109 A | 1/1981 |

* cited by examiner

*Primary Examiner* — Emily Schmidt
*Assistant Examiner* — Hamza Darb
(74) *Attorney, Agent, or Firm* — Hackler Daghighian & Martino

(57) ABSTRACT

A fluid warmer for tempering a medical fluid guided in a fluid line includes a first and second resistance heating element for alternating voltage and a heat exchanger thermally coupled to the two resistance heating elements and includes a holder for the fluid line. Each resistance heating element has a first and second electrical line connector, respectively, for connection of the resistance heating element to an alternating voltage source. Each electrical line connector has a respective drivable first switch. A respectively inversely phased alternating voltage or in-phase alternating voltage is applied to each resistance heating element during the tempering mode, wherein a compensation alternating voltage which is substantially inversely phased with respect to the heating alternating voltage is additionally applied to the heat exchanger using a compensation circuit. A voltage measurement device determines an electrical voltage between the heat exchanger and a neutral conductor of the alternating voltage source.

7 Claims, 3 Drawing Sheets

FLUID WARMER AND METHOD OF OPERATING A FLUID WARMER

CROSS-REFERENCE TO RELATED APPLICATIONS

This application claims priority to European Patent Application No. 13 154 381.1, filed Feb. 7, 2013, the entire contents of which are hereby incorporated by reference.

DESCRIPTION

1. Field of the Invention

The invention relates to a fluid warmer and a method of operating a fluid warmer for intravenous administration.

2. Background of the Invention

The application of large quantities of non-warmed fluids, for example, during the intravenous administration of blood products or infusion solutions, can have disadvantageous physiological effects, one reason for this being the associated loss of body heat.

In clinical practice, fluid warmers are therefore routinely used to pre-warm the medical fluid, which flows guided in the fluid line, to a temperature approximating the body temperature of usually 37° Celsius or to a higher temperature. In clinical practice, the fluid warmers must have a high thermal output in order to also reliably heat medical fluids at higher flow rates. The fluid warmers shall have a compact size in order to facilitate handling thereof, in particular in the form of mobile units or also in the form of attachment units for other medical devices or apparatuses. For this reason, the fluid warmers that are available on the market generally comprise resistance heating elements to be operated with alternating voltage or mains voltage and which do not require correspondingly dimensioned power supply units. Each resistance heating element is provided with a first and a second electrical line connector for electrically conductive connection of the resistance heating elements to an alternating voltage source (mains voltage). A heat exchanger that is thermally conductively connected (coupled) to the resistance heating elements is used for heat transfer to the fluid line and the medical fluid guided therein. For reasons of efficiency, the fluid line generally comprises a bag-shaped line section in order to ensure efficient heat transfer to the fluid. The heat exchanger is frequently plate-shaped, at least in sections, to ensure efficient heat transfer to the fluid line.

In practice, the tempered fluids come into electrically conductive contact with the person, typically bypassing the skin resistance. Resistance heating elements powered by alternating voltage, i.e., in particular mains voltage of 100 V to 240 V, can, due to capacitive coupling with other components of the fluid warmer, in particular, the heat exchanger, result in disturbances of other diagnostic or therapy devices, for example, ECG units, or also of organ structures which can be electrically stimulated, in particular, the heart. The fluid warmers used in the medical field must therefore, principally meet the high electrical safety requirements and the strict safety standards of the international uniform classification "CF" (abbreviation for cardiac floating). According to these, patient leakage currents, i.e., leakage currents conducted through a person in contact with the fluid, must not exceed a current conduction of a total of 10 μA (microamperes) under normal conditions and 50 μA in case of a fault.

It is the object of the invention to provide a fluid warmer of the above mentioned kind which meets the CF classification and has a simple structural design. Another object of the invention is to provide a method for operating such a fluid warmer that ensures a yet higher level of electrical operational safety. The present invention fulfills these needs and provides other related advantages.

SUMMARY OF THE INVENTION

The inventive fluid warmer comprises a first and a second resistance heating element for alternating voltage and a heat exchanger which is coupled to the two resistance heating elements and which comprises a holder for the fluid tube. Each resistance heating element has a first and a second line connector, respectively, for connecting the resistance heating element to an alternating voltage source. Each line connector of the two resistance heating elements, respectively, is provided with a first switch for conductively connecting the resistance heating elements to the alternating voltage source, or completely electrically separate them from the alternating voltage source, that is to overall stop an overall current flow via the line connectors of the resistance heating elements.

In accordance with the invention, respectively inversely phased alternating voltages can be applied to the resistance heating elements of the fluid warmer when the fluid warmer is in heating mode. Thus, in the heating mode, heating currents flow through the two resistance heating elements as ohmic consumers, the heating currents having a respectively inversely phased time behavior. For this reason, interference voltages in the heat exchanger due to capacitive interferences of the two resistance heating elements in the heat exchanger can completely or substantially cancel each other out. It is clear that, to this end, the resistance heating elements advantageously have corresponding electrical parameters and are arranged in a comparable position/orientation relative to the heat exchanger. It should be noted that this solution does, of course, require an internal alternating voltage source within the device which provides an alternating voltage for heating one of the resistance heating elements, the alternating voltage being phase-shifted by exactly or almost exactly 180° with respect to the alternating voltage of the other resistance heating element.

In accordance with the invention, it is also possible to apply respectively in-phase alternating voltages to the resistance heating elements during the tempering mode, i.e. respectively in-phase alternating voltages are applied to the resistance heating elements during the tempering. Heating currents with respectively in-phase time behavior consequently flow through the resistance heating elements during temperature control. In this case, the fluid warmer comprises a compensation circuit for compensating the capacitive interference of the resistance heating elements in the heat exchanger, which compensation circuit enables application of a compensation alternating voltage to the heat exchanger which is substantially inversely phased with respect to the alternating voltage of the resistance heating elements. In this connection, the compensation circuit advantageously only has to provide that power that is, in fact, generated by the interferences in the heat transfer element. The required compensation power P for a fluid warmer having e.g. an electrical power of 400 W and a capacitive leakage (leakage current) of e.g. 88 μA would then be P=230 VAC·88 μA=0.02 W.

The capacitive interference in the heat exchanger and accordingly in the fluid line or the medical fluid guided therein, which is associated with the tempering operation of the resistance heating elements, can be completely or substantially compensated for with both above-mentioned electric modes of operation of the resistance heating elements.

In accordance with the invention, the fluid warmer furthermore has a measuring device for determining a voltage between the heat exchanger and a neutral conductor of the alternating voltage source or a component of the fluid warmer, which is electrically conductively connected to the neutral conductor. Here, the measuring device is advantageously designed for continuously determining or measuring the voltage.

In accordance with the invention, the fluid warmer furthermore comprises a control device for controlling the modes of operation of the fluid warmer. The control device is preferably designed to transfer the first switches synchronously into their open switching state in dependence on the voltage between the heat exchanger and the neutral conductor of the alternating voltage source. For this reason, in the event of a fault, i.e. when e.g. a mains voltage is applied to a person who is electrically conductively connected to the fluid line, e.g. due to a fault of a device that is operated at the same time as the fluid warmer (so-called "SFC" fault condition), a leakage current that is potentially dangerous for the person and would be transferred capacitively from the fluid to the heat exchanger and from the latter (capacitively) to the resistance heating elements and be conducted via the neutral conductor of the alternating voltage source, can be prevented. Moreover, an undesired leakage current originating from the fluid warmer, e.g. due to a malfunction of the fluid warmer, can be detected at an early stage and be eliminated. This is advantageous for the overall electrical operational safety of the fluid warmer. In the present case, the open switching state of the switches is understood to be the switching state in which conduction of current through the switches is interrupted. The defined time interval within which the switches are transferred to their open switching state will always be set such that a hazard to the patient due to residual or patient leakage currents can be positively obviated. The inventive fluid warmer does meet the relevant standard of the international safety classification "CF" (abbreviation for "Cardiac Floating") without requiring separate functional earth of the heat exchanger assembly. This offers advantages in design.

In accordance with the invention, the above explained compensation circuit may also be provided for the application of respectively inversely phased alternating voltages to the resistance heating elements as explained above. The capacitive loading of the heat exchanger due to interferences of the resistance heating elements (and the accompanying undesired leakage currents) that occurs despite the inversely phased alternating voltage operation of the resistance heating elements may thus be compensated for completely or almost completely. This may be required e.g. when the electrical properties of the resistance heating elements are not matched perfectly to each other.

The compensation circuit may, in particular, have an electrical LC resonant circuit having an inductor L and a capacitor C that is connected to the heat exchanger. The capacitor and the inductor may be connected, in particular, in series. The inductor, in the simplest design case, may be constituted by the secondary side of a transformer T, which is electrically switched in parallel to the resistance heating element on its primary side. In this case, the primary side of the transformer is connected to the electrical line connectors of at least one resistance heating element (i.e. is switched in parallel with the resistance heating element) and may therefore be powered from the alternating voltage source simultaneously with the resistance heating elements. In this way, the LC resonant circuit can be excited to (forced) electrical oscillations having a frequency corresponding to the alternating or mains voltage. Due to the phase shift of the current thus produced in the LC resonant circuit, the (capacitive) leakage current of the heat exchanger induced by the simultaneous operation of the resistance heating element can be largely compensated for. This further reduces any potential hazard to the patient. The resonant circuit described above can also be configured with electronic components (e.g. using a microprocessor).

Alternatively, the compensation circuit may also comprise a so-called phase-locked loop or a phase shifter which is known per se.

In accordance with the invention, the fluid warmer advantageously comprises a polarity switch by means of which the electrical line connectors with a predetermined polarity can be connected to the alternating voltage source. This enables compensation of capacitive interference of the resistance heating elements in the heat exchanger without requiring further monitoring/polarity switching at the input side of the compensation circuit.

The measuring device may, in particular, comprise a comparator circuit which is realized by hardware and by means of which the electric voltage between the heat exchanger and the neutral conductor of the alternating voltage source can be detected.

For regulating the tempering process, the fluid warmer advantageously has a temperature measurement device with a temperature sensor associated with the heat exchanger. Preferably, the temperature sensor is connected to an evaluation and/or display unit via an electrically conducting connecting line. In this case, the electrical operational safety of the fluid warmer can be further increased in accordance with the invention in that the electrical connecting line comprises one or more drivable switches for each connection conductor, which switches may be transferred into their open switching state, preferably via the control device, simultaneously with the first switches of the line connectors of the resistance heating elements.

In accordance with a preferred further development of the invention, the heat exchanger is functionally grounded. In this way, a local equipotential can additionally be established in the region of the heat exchanger, in particular in case of incomplete compensation of the capacitive interference in the heat exchanger, thereby preventing leakage currents from being conducted via the medical fluid as so-called patient leakage currents. This even further increases the reliability with which the danger of cardiac dysrhythmia or also disturbances of other medical apparatuses and devices, such as an ECG unit or an internal/external defibrillator is counteracted.

In this case, the heat exchanger is electrically conductively connected to a functional grounding conductor (FE). The functional grounding conductor advantageously has a third switch that can preferably be driven by the control device. In the event of a fault, the switch of the functional grounding conductor can be transferred jointly (synchronously) with the first switches of the line connectors of the resistance heating elements and, if existing, with the second switch of the temperature measurement device, into the open switching state. In this way, undesired flows of dangerous leakage currents ("SFC" fault condition) via the functional grounding conductor can be effectively prevented in the event of a fault.

It should be noted that in case of incomplete compensation of the leakage currents capacitively induced in the heat exchanger through the tempering operation of the resistance elements, there is always an, albeit small, leakage current that flows via the functional grounding conductor. In accordance with the invention, the control device can comprise a sensor for detecting the leakage current IA via the functional grounding conductor. The control device is advantageously programmed to monitor the functional integrity of the functional grounding conductor and/or the efficiency of the compensation device on the basis of the conduction or the leakage current that is present. A drop of the leakage current discharged via the functional grounding conductor to or below a predetermined minimum threshold current Imin can either be an indication of a severe malfunction (short circuit) of a device that is used on a person simultaneously with the fluid warmer or to an interrupted functional grounding conductor. For technical measurement reasons, the functional grounding conductor is preferably provided with a dropping resistor that is connected upstream of the sensor.

According to the invention, the drivable first, second and/or third switches can be constituted, in particular, as electronic switches, for example, as TRIACs (bidirectional triode thyristors), or MOSFETs (metal-oxide semiconductor field-effect transistors). These are readily available on the market and are therefore available at low cost. With electronic switches, especially short switching periods can be achieved. As they have no switching contacts, wear of the switches and unwanted bouncing effects can be avoided in this way, too. In a further embodiment of the invention, the switches can also be constituted, at least in part, as relays.

According to the invention, the time interval within which the switches can be transferred into their open switching state is preferably geared to the period of the alternating voltage provided by the alternating current source. Here the time interval is in any case shorter than a period T, preferably shorter than a half-period $T_{half}$ of the alternating voltage (=line voltage) provided by the alternating voltage source. For example, the maximum switching time of the switches for an alternating voltage with 50 Hz is preferably less than 10 ms, especially preferably less than 1 ms.

To take account of safety aspects, it has moreover turned out to be advantageous for each switch to be duplicated, i.e. designed as two series-connected single switches each, which can be operated synchronously.

The switches can preferably be transferred into their open switching state at a voltage that corresponds to a defined threshold voltage value or is larger than the threshold voltage value. The threshold voltage value can, in particular, be a 132 Volt alternating voltage and is preferably stored in the control device.

In accordance with the invention, in the simplest structural design, the heat transfer element of the fluid warmer can comprise two or more heat transfer plates forming the holder for the fluid tube therebetween. The heat transfer plates can thereby be movable with respect to each other in a manner known per se or be arranged stationarily with respect to each other on a heat plate support of the fluid warmer. The holder can e.g. be an insertion channel for a reservoir-like line section of the fluid line such as e.g. a fluid bag or a fluid cartridge. This permits a large contact surface of the heat exchanger with the fluid line and therefore optimum heat transfer to the fluid flowing therein.

For efficient tempering of the medical fluid, it is preferred that the fluid warmer has a power output of at least 0.25 kilowatts, preferably of greater than 0.35 kilowatts, in particular approximately 0.4 kilowatts.

The inventive method enables particularly reliable and safe operation of the inventive fluid warmer. The invention is explained further below using an example depicted in the drawing. The embodiments shown and described are not to be understood as an exhaustive account but are rather examples used to describe the invention.

In summary, an exemplary embodiment of the present invention discloses a fluid warmer for tempering of a medical fluid guided in a fluid line including a first and a second resistance heating element for alternating voltage, a heat exchanger thermally coupled to the first and second resistance heating elements, the heat exchanger comprising a holder for the fluid line, wherein each resistance heating element has a first and a second electrical line connector, respectively, for connection of the resistance heating elements to an alternating voltage source, wherein each electrical line connector, respectively, of the first and second resistance heating elements includes a first and second drivable switch, a voltage measurement device connected to the heat exchanger and a neutral conductor of the alternating voltage source for determining a voltage between the heat exchanger and the neutral conductor of the alternating voltage source; and a control device connected to the first and second drivable switch for synchronized transfer of the switches into their open switching state in dependence on the voltage, wherein a respectively inversely phased alternating voltage is applied to each resistance heating element during a tempering mode or wherein respectively in-phase alternating voltages are applied to the resistance heating elements during the tempering mode and a compensation alternating voltage, which is substantially inversely phased with respect to the alternating voltage, is applied to the heat exchanger using a compensation circuit.

In other exemplary embodiments, the compensation circuit may include an LC resonant circuit, a phase-locked loop or a phase shifter.

A polarity switch may be connected to the first and second electrical line connector for switching a respective polarity of the electrical line connectors from the alternating voltage source.

The first and second drivable switches may be transferable into their open switching state at the voltage which is equal to or larger than a defined threshold voltage value stored in the control device.

A temperature measurement device may include an evaluation unit, the evaluation unit being connected to a temperature sensor via an electrical connecting line, where the temperature sensor is arranged on or in the heat exchanger, wherein the connecting line includes a third drivable switch which is transferable into its open switching state synchronously with the first and second drivable switches of the first and second electrical line connectors.

The heat exchanger may be electrically conductively connected to a functional grounding conductor, wherein the functional grounding conductor is provided with a fourth drivable switch, which is transferable into its open switching state synchronously with the first and second drivable switches of the first and second electrical line connectors or with the third drivable switch of the temperature measurement device.

The control device may include a current measurement device detecting a leakage current via the functional grounding conductor. The control device may be programmed to jointly transfer the switches into the open switching state on occurrence of a leakage current via the functional grounding conductor, which is equal to or less than a defined minimum threshold current conduction.

The first and second drivable switches may be field-effect transistors or relays.

The heat exchanger may include two heat transfer plates forming the holder for the fluid tube therebetween.

A method for controlling the fluid warmer may include detecting the voltage between the heat exchanger and the neutral conductor of the alternating voltage source and transferring the first and second drivable switches of the first and second electrical line connectors in their open switching state provided that the voltage is equal to or larger than a predetermined threshold voltage value.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
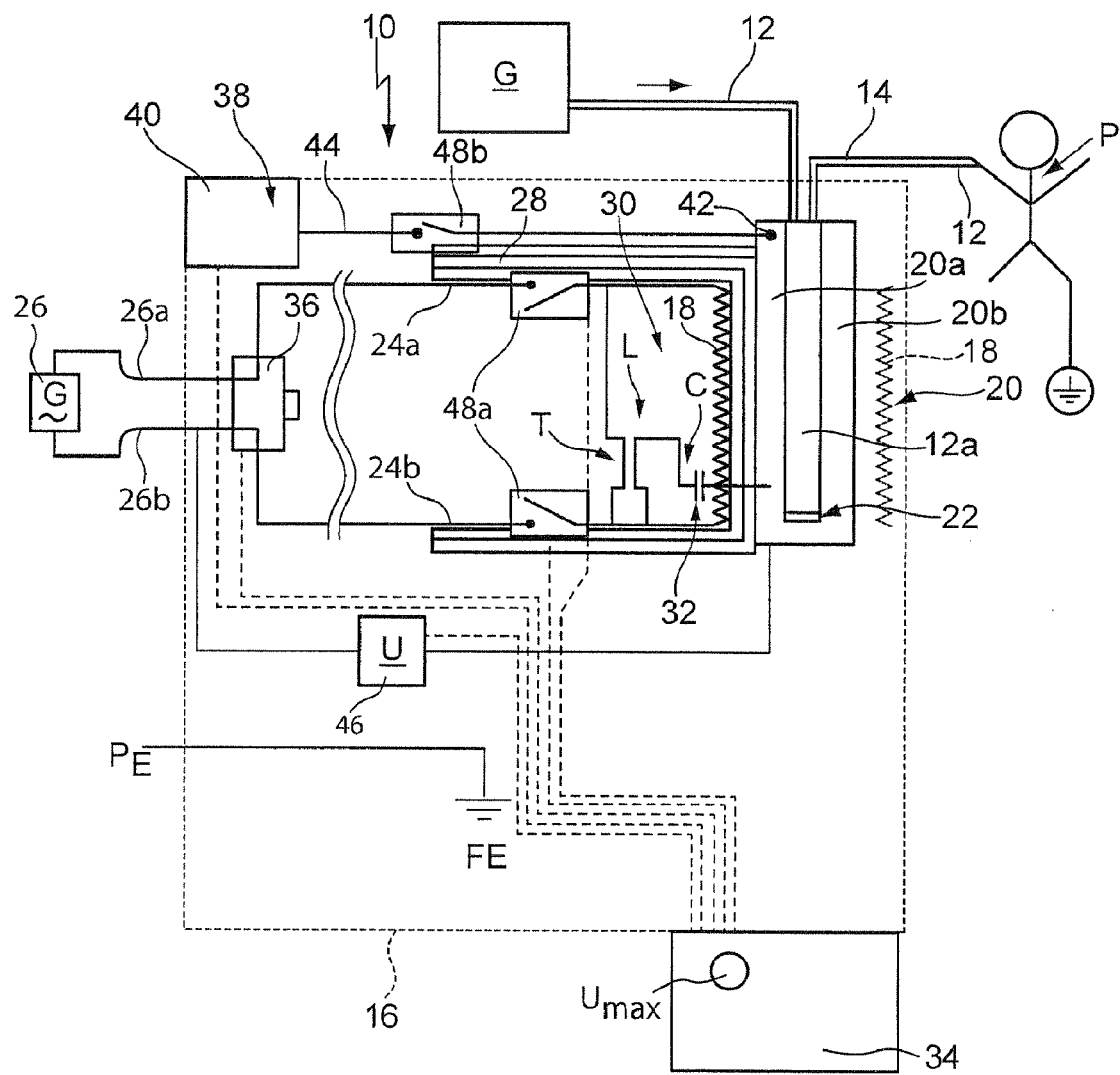
FIG. 1 is a block diagram of an inventive fluid warmer for tempering of a fluid guided in a fluid line, including two resistance heating elements with electrical line connectors for an alternating voltage source and a heat exchanger, the electrical line connectors being provided with switches which can be transferred into their switching state, in which they do not carry a current, in dependence on an electrical voltage between the neutral conductor of the alternating voltage source and the heat exchanger.

FIG. 1 shows a fluid warmer 10 for tempering of a medical fluid 14 guided in a fluid line 12. The fluid warmer 10 has a housing 16 with two resistance heating elements 18 which are disposed at a distance from each other in the housing 16 and are thermally coupled to a heat exchanger 20, i.e. thermally conductively connected thereto. The resistance heating element 18 illustrated on the right-hand side in FIG. 1 is only indicated by a dashed line for reasons of illustration. In this case, the resistance heating elements 18 are each constituted by a heating coil, but they can also have a different shape.

The heat exchanger 20 has two heat exchanging plates 20a, 20b which are disposed parallel and at a distance from each other to form a holder 22. A bag-shaped expanded line section (fluid bag) 12a of the fluid line 12 is pushed or laid into the holder 22. The line section 12a is essentially in contact with the two heat exchanging plates 20a, 20b of the heat exchanger 20 with its full surface. This ensures optimum heat transfer to the flowing fluid 14 guided in the fluid tube.

The fluid line 12 is constituted by an infusion line known per se in the medical sector and is made of plastic. At one end, the fluid line is connected to the blood circulation (not shown) of a person P to be treated, e.g. via a venous access/vein indwelling catheter that is not depicted in any further detail. In this case, the fluid 14 is therefore in electrically conductive contact with the blood circulation of the person P, bypassing the usually high electrical resistance of the skin. G designates a further (medical) device which can e.g. be configured as a dialysis unit. The device G is simultaneously operated with the fluid warmer and is connected to the fluid warmer/person P via the fluid line 12.

Each resistance heating element 18 has a first and a second electrical line conductor 24a, 24b, which are used for electrically connecting the resistance heating element 18 to a mains voltage, i.e., to an external alternating voltage source 26. The electrical line connectors of the resistance heating element 18 illustrated on the right-hand side in the figure are not illustrated.

The alternating voltage source 26 provided to power the resistance heating elements 18 has an operating voltage which usually is country-specific of, for example, 230 V±10% and a mains frequency of approximately 50 Hz.

In this case, the electrical line connector 24a, which is the upper of the two in the figure, of the resistance heating elements 18 is electrically conductively connected to an outer connector 26a of the alternating voltage source, while the second electrical line connector 24b is electrically conductively connected to a neutral conductor 26b of the alternating voltage source 26.

The two electrical line connectors 24a, 24b and the respective resistance heating element 18 form a mains supply circuit of the fluid warmer 10 that is electrically isolated from the patient P or a user by means of a reinforced, here double, insulation 28. The insulation 28 of the resistance heating element 18 illustrated on the right-hand side in the figure is not shown for illustrative reasons.

In the illustrated embodiment, an alternating voltage (mains voltage) is applied to each of the two resistance heating elements 18 during the tempering mode of the fluid warmer 10. The two alternating voltages are thereby in-phase with respect to each other such that respectively in-phase heating currents flow through the resistance heating elements 18 during the tempering mode.

An electrical compensation device, in the present case a compensation circuit 30 is used to compensate for capacitive interference of the resistance heating elements 18 in the heat transfer element 20, which is unavoidable during the tempering mode of the fluid warmer 10. The compensation circuit 30 has an LC resonant circuit 32 with an inductor L and a capacitor C. The LC resonant circuit is connected to the heat exchanger and the electrical line connector, which is connected to the neutral conductor of the alternating voltage source. In this case, the inductor L and the capacitor C of the LC resonant circuit 32 are connected in series. The inductor L is constituted by a secondary side of a transformer T, whose primary side is connected to the two electrical line connectors 24a, 24b of the resistance heating elements 18. When the resistance heating elements 18 and the transformer T are jointly powered by the mains voltage of the alternating voltage source 26, the LC resonant circuit is excited to electrical oscillations. Because of a (predetermined) phase shift of the current in the LC resonant circuit (of approximately 180°) with respect to the heating current of the resistance heating elements 18, the capacitive interference of the resistance heating elements in the heat transfer element 20 is completely or substantially compensated for. The resonant circuit described above can also be configured with electronic components (e.g. using a microprocessor).

A control device 34 with a display and operator panel which is not shown in detail is used in this case to control all operating parameters of the fluid warmer 10. The control device 34 is programmed to detect the polarity at the mains input side of the electrical line connectors 24a, 24b at the alternating voltage source 26. The polarity of the line connectors 24a, 24b can be changed to the (predetermined) polarity illustrated in FIG. 1 by means of a polarity switching device 36 controlled by the control device. In this way, the compensation function of the compensation circuit is guaranteed irrespective of mechanical connection of the electrical line connectors 24a, 24b.

The temperature of the heat exchanger 20 is monitored by a temperature measurement device 38 with an evaluation unit 40 and a temperature sensor 42 arranged on or in the heat exchanger 20. The temperature sensor 42 is connected to the evaluation unit 40 via an electrically conducting connecting line 44. The temperature measurement device 38 may be part of the control device 34.

The control device 34 has a voltage measurement device 46 by means of which an electrical voltage U between the heat exchanger 20 and the neutral conductor 26b of the alternating voltage source 26 can be detected or monitored.

As shown in FIG. 1, the two electrical line connectors 24a, 24b of the resistance heating elements 18 are provided with drivable first switches 48a and the connecting line 44 of the temperature measurement device 38 is provided with drivable second switches 48b. The switches 48a, 48b can each be switched between a switched-on (closed) and a switched-off (open) switching state shown in the Figure. In the closed switching state, the switches 48a, 48b are conductive, i.e. their switch input is electrically conductively connected to the switch output with low resistance. In the open switching state, the switches are non-conductive, i.e., their inputs and outputs are electrically isolated from each other in the open switching state. In this case, the switches 48a, 48b are constituted by relays but can also be constituted by MOSFETs (metal-oxide-semiconductor field-effect transistors), by TRIACs (bidirectional triode thyristors), or the like. The switches 48a, 48b can be actuated by the control device 34. The predetermined time interval within which the switches 48a, 48b can be transferred into their open switching state by the control device 34 is always shorter than a period, preferably shorter than a half period, of the alternating voltage of the alternating voltage source 26 used for operating the resistance heating elements 18. The time interval is, in particular, less than 10 ms for a mains frequency of 50 Hz.

A threshold voltage value Umax is deposited (stored) in the control device 34 for the electrical voltage between the heat exchanger and the neutral conductor 26b of the alternating voltage source 26. The control device 34 is programmed to transfer the switches 48a, 48b into their open switching state as soon as the voltage U between the heat exchanger and the neutral conductor 26b reaches or exceeds the threshold voltage value Umax. In this way, discharge of an undesired leakage current from the heat exchanger 20 via the resistance heating elements 18 or the temperature measurement device 38 and the neutral conductor 26b of the alternating voltage source 26 can be prevented in a fault condition (SFC). Moreover, further capacitive coupling of the resistance heating elements 18 into the heat exchanger 20 and the fluid 14 guided therein is prevented. This reliably counteracts an undesired leakage current of the fluid warmer via the fluid line.

In one embodiment of the fluid warmer 10, which is not shown in detail, respectively inversely phased alternating voltages are applied to the two resistance heating elements 18 during tempering. In this case, the above described compensation circuit can be omitted. A phase shifter or the like can be used for generating an alternating voltage that is inversely phased with respect to the alternating voltage applied to a resistance heating element 18.

Figure 2:
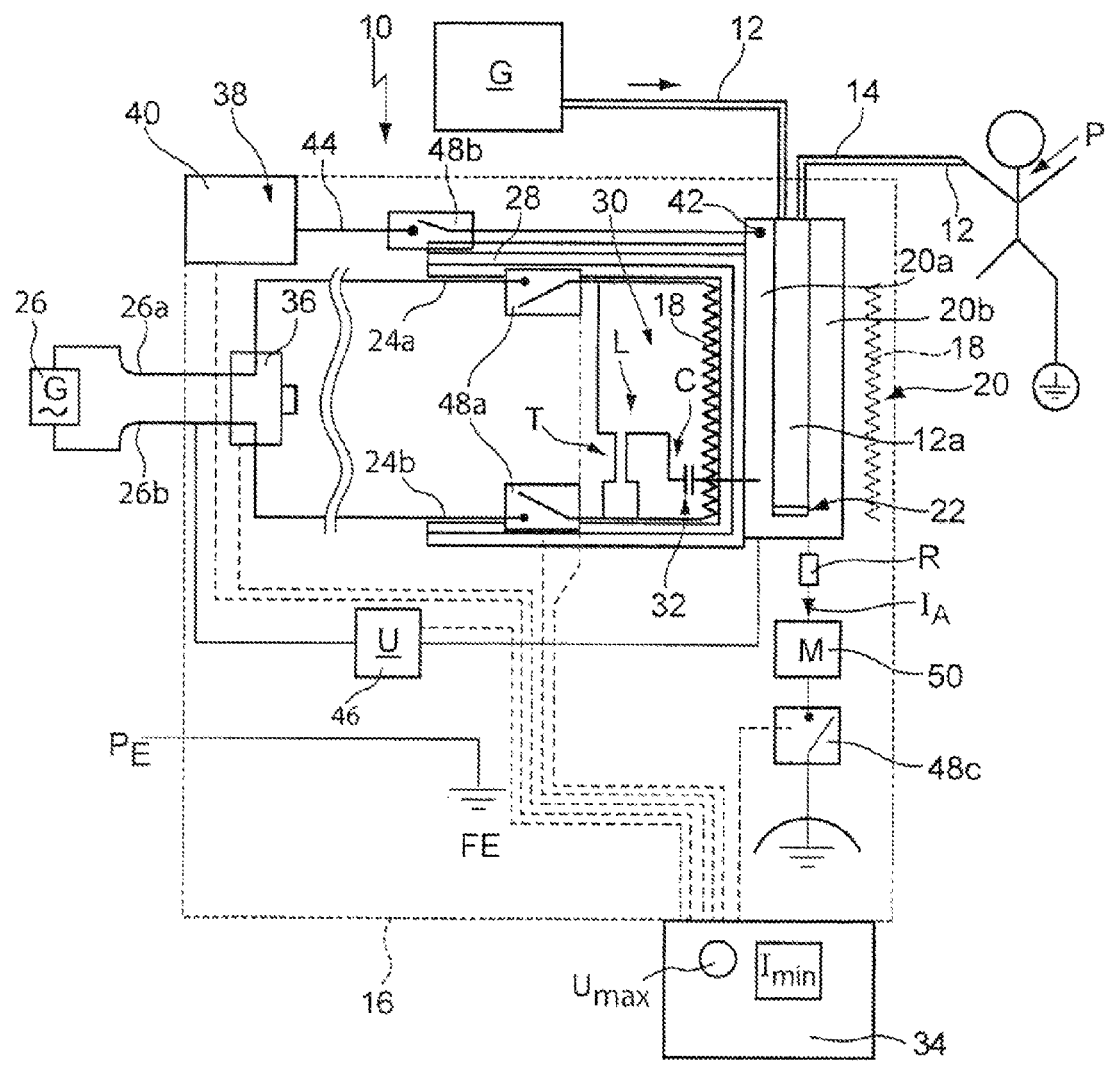
FIG. 2 a block diagram of a fluid warmer, the heat transfer element of which is additionally functionally grounded.

FIG. 2 shows a fluid warmer 10 which differs from the fluid warmer 10 explained in connection with FIG. 1 substantially in that the heat transfer element 20 is functionally grounded by means of a functional grounding conductor FE. The functional grounding conductor FE is electrically conductively connected to protective earth PE of the fluid warmer 10. The functional grounding conductor FE is connected to a third switch 48c which can be driven by the control device. The drivable third switch can have the same construction as the other switches 48a, 48b. A current measurement device 50 is connected to the control device 34 and is used to detect the leakage current I discharged via the functional grounding conductor. A dropping resistor R is connected upstream of the current measurement device 50. In case of incomplete compensation of the capacitive interferences of the resistance heating elements 18 in the heat exchanger 20 during tempering of the fluid warmer 10, a small leakage current IA will principally flow via the functional grounding conductors FE. In the present case, the control device 34 is programmed to compare the leakage current IA with a minimum threshold current conduction Imin stored in the control device 34 and, if the leakage current IA is smaller than or equal to the minimum threshold current magnitude Imin, to jointly transfer the controllable first, second and third switches 48a, 48b, 48c into their open switching state within the predetermined switching period.

Figure 3:
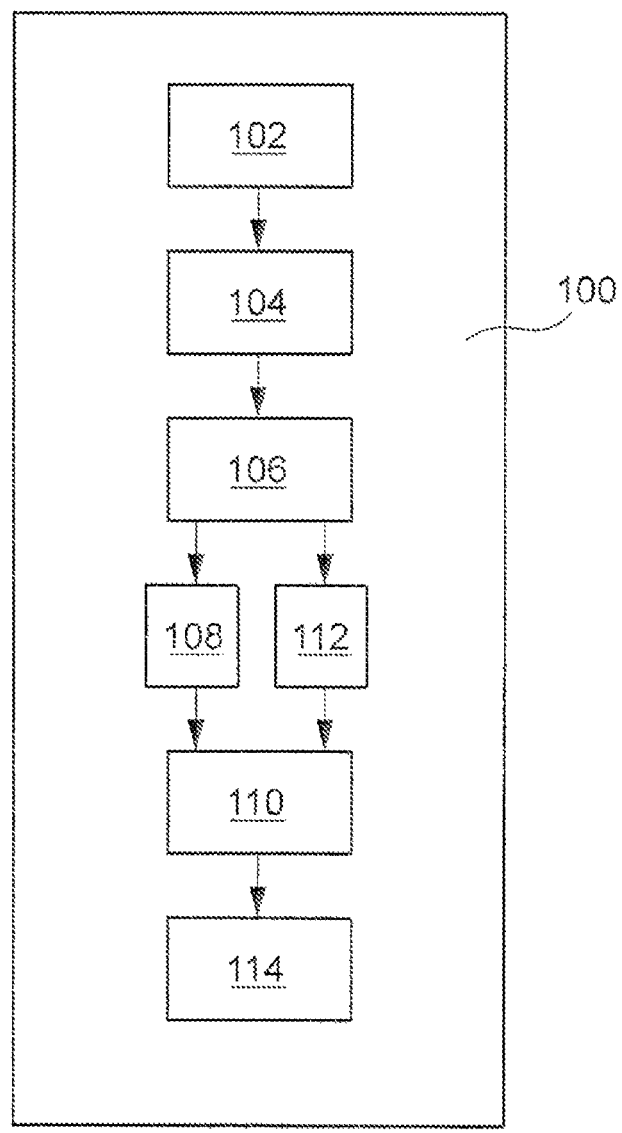
FIG. 3 a diagram of an inventive method for operating the fluid warmers illustrated in FIGS. 1 and 2.

The inventive method 100 of operating the fluid warmer 10 from FIGS. 1 and 2 is explained below with additional reference to FIG. 3.

The control device 34 (FIGS. 1, 2) of the fluid warmer 10 is programmed to perform the individual steps of the method. The control device 34 can however also permit the method 100 to be performed purely by virtue of its hardware configuration.

After the fluid warmer 10 has been connected 102 to the alternating voltage source 26 and the fluid warmer 10 has been switched on, the control device 34 is initially in a standby mode.

Prior to start of tempering of the fluid warmer 10, the polarity of the electrical line connectors 24a, 24b with respect to the alternating voltage source 26 is determined in a further step 104 and compared with the predetermined polarity. When the polarity of the line connectors 24a, 24b with respect to the outer conductor 26a and the neutral conductor 26b of the alternating voltage source 26 differs from the predetermined polarity, the control unit 34 changes the polarity to the predetermined polarity illustrated in FIGS. 1 and 2 by means of the polarity switch 36.

For initiating the tempering mode, the first switches of the two electrical line connectors 24a, 24b are closed in a further step 106. It should be noted that the intermittent "switching off" and "on" of the resistance heating elements 18 is required in the tempering mode. To this end, merely the drivable first switches 48a of the electrical line connectors 24a which are connected to the outer conductor 26a of the alternating voltage source 26 are driven by the control device 34 during normal operation of the fluid warmer.

During the tempering mode of the fluid warmer 10, the voltage U between the heat transfer element 20 and the neutral conductor 26b of the alternating voltage source 26 is continuously detected by the voltage measurement device 46 in a further step 108 and the control device 34 compares the detected voltage U with the threshold voltage value Umax stored in the control device 34.

As soon as the voltage U reaches or exceeds the threshold voltage value Umax, the switches 48a, 48b, 48c are jointly transferred in their open switching state within the defined time period in a further step 110 so that the fluid warmer 10 is in an activated mode of protection.

If the fluid warmer 10 is provided with a functionally grounded heat exchanger 20, the control device additionally monitors the leakage current IA that flows via the functional grounding conductor FE during tempering of the fluid warmer 10 in step 112. As soon as a state is reached in which the leakage current IA is equal to or smaller than the minimum threshold current conduction Imin, this state is assessed as a disturbance (interruption) of the functional grounding conductor and the control device 34 transfers the switches 48a, 48b, 48c in step 110 into their open switching state. In the standalone mode of operation of the fluid warmer 10, faulty functional grounding FE of the heat exchanger 20 can thus be detected and a hazard for the patient P due to undesirably high patient leakage currents can be counteracted. Furthermore, when the fluid warmer 10 is simultaneously used with a further device 6 on the patient P, disturbances of the other device G can be detected in which capacitive leakage currents are mainly or solely conducted via the other device G. The fluid warmer 10 is, here too, in its activated mode of protection. In a further step 114, the activated mode of protection of the fluid warmer 10 can be optically and/or acoustically displayed on the fluid warmer 10 to an operator by means of a signal generator.

In summary, a fluid warmer for tempering a medical fluid guided in a fluid line includes a first and a second resistance heating element for alternating voltage and a heat exchanger which is thermally coupled to the two resistance heating elements and includes a holder for the fluid line. Each resistance heating element has a first and a second electrical line connector, respectively, for connection of the resistance heating element to an alternating voltage source. Each electrical line connector has a respective drivable first switch. A respectively inversely phased alternating voltage or in-phase alternating voltage is applied to each resistance heating element during the tempering mode, wherein a compensation alternating voltage which is substantially inversely phased with respect to the heating alternating voltage is additionally applied to the heat exchanger using a compensation circuit. A voltage measurement device is used to determine an electrical voltage between the heat exchanger and a neutral conductor of the alternating voltage source. The fluid warmer has a control device for synchronized transfer of the drivable first switches into their open switching states in dependence on the electrical voltage. The invention also relates to a method of operating such a fluid warmer. Further advantages and advantageous embodiments of the object of the invention result from the description, the claims, and the drawing.

Although several embodiments have been described in detail for purposes of illustration, various modifications may be made to each without departing from the scope and spirit of the invention. Accordingly, the invention is not to be limited, except as by the appended claims.

What is claimed is:

1. A fluid warmer for tempering of a medical fluid guided in a fluid line, the fluid warmer comprising:
   a first and a second resistance heating element for alternating voltage;
   a heat exchanger thermally coupled to the first and second resistance heating elements, the heat exchanger comprising a holder for the fluid line;
   wherein each resistance heating element has a first and a second electrical supply connection conductor, respectively, for connection of the resistance heating elements to an alternating voltage source;
   wherein the first electrical supply connection conductor includes a first drivable switch and wherein the second electrical supply connection conductor includes a second drivable switch;
   a voltage measurement device connected to the heat exchanger and a neutral conductor of the alternating voltage source for determining a voltage between the heat exchanger and the neutral conductor of the alternating voltage source;
   a control device connected to the first and second drivable switch for synchronized transfer of the switches into their open switching state in dependence on the voltage;
   a temperature measurement device comprising an evaluation unit, the evaluation unit being connected to a temperature sensor via an electrical connecting line, where the temperature sensor is arranged on or in the heat exchanger, wherein the connecting line includes a third drivable switch which is transferable into its open switching state synchronously with the first and second drivable switches of the first and second electrical supply connection conductors;
   wherein the heat exchanger is electrically conductively connected to a functional grounding conductor, wherein the functional grounding conductor is provided with a fourth drivable switch, which is transferable into its open switching state synchronously with the first and second drivable switches of the first and second electrical supply connection conductors or with the third drivable switch of the temperature measurement device;
   wherein the control device includes a current measurement device detecting a leakage current via the functional grounding conductor;
   wherein the control device is programmed to jointly transfer the switches into the open switching state on occurrence of a leakage current via the functional grounding conductor, which is equal to or less than a defined minimum threshold current conduction; and
   wherein a respectively inversely phased alternating voltage is applied to each resistance heating element during a tempering mode; or
   wherein respectively in-phase alternating voltages are applied to the resistance heating elements during the tempering mode and a compensation alternating voltage, which is substantially inversely phased with respect to the alternating voltage, is applied to the heat exchanger using a compensation circuit.

2. The fluid warmer according to claim 1, wherein the compensation circuit comprises an LC resonant circuit.

3. The fluid warmer according to claim 1, wherein the compensation circuit comprises a phase-locked loop or a phase shifter.

4. The fluid warmer according to claim 1, including a polarity switch connected to the first and second electrical supply connection conductor for switching a respective polarity of the electrical supply connection conductors from the alternating voltage source.

5. The fluid warmer according to claim 1, wherein the first and second drivable switches are transferable into their open switching state at the voltage which is equal to or larger than a defined threshold voltage value stored in the control device.

6. The fluid warmer according to claim 1, wherein the first and second drivable switches are field-effect transistors or relays.

7. The fluid warmer according to claim 1, wherein the heat exchanger includes two heat transfer plates forming the holder for the fluid tube therebetween.

* * * * *